United States Patent [19]

Matsuda et al.

[11] 4,456,760

[45] Jun. 26, 1984

[54] PROCESS FOR THE PREPARATION OF INDOLES

[75] Inventors: Fujio Matsuda, Kanagawa; Takazo Kato, Ohimachi; Tadamitsu Kiyoura, Kanagawa, all of Japan

[73] Assignee: Mitsui Toatsu Chemicals, Incorporated, Tokyo Japan

[21] Appl. No.: 374,919

[22] Filed: May 5, 1982

Related U.S. Application Data

[63] Continuation-in-part of Ser. No. 254,457, Apr. 15, 1981, abandoned.

[51] Int. Cl.$^3$ .......................................... C07D 209/08
[52] U.S. Cl. .................................................... 548/508
[58] Field of Search ........................................ 548/508

[56] References Cited

U.S. PATENT DOCUMENTS

| | | | |
|---|---|---|---|
| 3,699,120 | 10/1972 | Bakke et al. | 548/508 |
| 3,984,434 | 10/1976 | O'Murchu | 548/508 |

FOREIGN PATENT DOCUMENTS

| | | | |
|---|---|---|---|
| 50-197608 | 3/1975 | Japan | 260/319.1 |
| 54-105663 | 2/1979 | Japan | 260/319.1 |
| 55-108850 | 8/1980 | Japan | 548/508 |
| 56-36451 | 4/1981 | Japan | 548/508 |

OTHER PUBLICATIONS

J. A. C. S., Heine et al., "The Synthesis of Some N-Arylethylenimine", 76, 2503, (1954), p. 2503.
Ind. Eng. Chem., Prod. Res. Dev., vol. 15, No. 3, 1976, Bhattacharyya and Nandi, "Synthesis of N-N-Dimethylaniline from Aniline and Methanol", pp. 201-206.
Chemical Abstracts, 66, 75974s, (1967), pp. 7126-7127.
Chemical Abstracts, 70, 78437n, (1969), p. 6.
Ind. Eng. Chem., 43, (7), 1579, (1951), Catalytic Reactions of Aromatic Amines, Alkylation with Alcohols, Hill et al.
Chemical Abstracts, 82, P170329z, (1975), Governale et al.
J. A. C. S., 101:2, Jan. 17,1979, "Reactions of Aniline with Olefins Catalyzed by Group 8 Metal Complexes: N-Alkylation and Heterocycle Formation".
"Classification of Catalysts by Reactions", Edited by Tarama Laboratory Staff of Kyoto University, Japan, published by Kagaku Kogyo Sha, (Chemical Industrial Co.), of Tokyo, Japan, pp. 74–76, (Sep. 1, 1971), (with translation).

*Primary Examiner*—Paul M. Coughlan, Jr.
*Assistant Examiner*—D. B. Springer
*Attorney, Agent, or Firm*—Fisher, Christen & Sabol

[57] ABSTRACT

A process for the preparation of indole and derivatives thereof wherein an aniline is reacted with a 1,2-glycol in the liquid phase in the presence of a catalyst containing metallic copper and/or copper oxide. The present invention makes it possible to prepare indole and derivatives thereof in a single step by using inexpensive starting materials.

9 Claims, No Drawings

PROCESS FOR THE PREPARATION OF INDOLES

CROSS-REFERENCE TO RELATED APPLICATION

This application is a continuation-in-part of our application Ser. No. 254,457, filed on Apr. 15, 1981, now abandoned.

BACKGROUND OF THE INVENTION (1) Field of the Invention

This invention relates to a novel process for the preparation of indole and derivatives thereof by reacting an aniline with a 1,2-glycol in the liquid phase in the presence of a copper-containing catalyst.

(2) Description of the Prior Art

In the prior art, indole derivatives have long been prepared by the well-known Fischer indole synthesis in which phenylhydrazine is reacted with a compound having an aldehyde group. If the aldehyde compound is other than acetaldehyde, the aforesaid Fischer indole synthesis can be applied to obtain indole derivatives in good yield. However, if the aldehyde compound is acetaldehyde, no reaction that yields indole has been believed to take place. In order to overcome this disadvantage, there has recently been proposed an improved process which comprises reacting phenylhydrazine with acetaldehyde at an elevated temperature of from 300° to 400° C. in the presence of an alumina catalyst (Japanese Patent Laid-Open No. 76864/'73).

This process permits the reaction to proceed and brings about the formation of indole, but fails to give a satisfactory yield. Moreover, it is greatly disadvantageous in that the catalyst has so short a life as to become totally inactive after 0.5–1 hour's use.

Indole can also be prepared by another process which comprises reacting o-toluidine with formic acid to form o-methyl-N-formylaniline and then fusing it together with potassium hydroxide. However, it is usually impossible to selectively prepare o-toluidine that is used as the starting material in this process. That is, the p-isomer is always formed in an amount equal to or greater than that of the o-isomer. Thus, treatment of the isomer formed as a by-product poses a serious problem in the case of industrial production. Moreover, the handling of solids as in alkali fusion is troublesome. For these reasons, the aforesaid process cannot be regarded as suitable for industrial purposes.

Furthermore, a number of attempts have been made to synthesize indole from N-β-hydroxyethylamine, but none of them are satisfactory from an industrial point of view. For example, a process which comprises effecting the reaction at 300° C. in the presence of an aluminosilicate catalyst [Zhur. Obschue. Khim., Vol. 24, pp. 671–678 (1954)] gives only a very low yield of indole. A process which comprises heating the reactant together with a molten mixed salt consisting mainly of zinc chloride (Japanese Patent Laid-Open No. 57968/'73) can give a fairly high yield of indole. However, this process has the disadvantage of requiring a complicated procedure, which makes it unsuitable for industrial purposes.

As described above, a number of processes for the synthesis of indole and derivatives thereof have been proposed. However, many of them are disadvantageous in that amounts of by-products are formed, expensive compounds are used as the starting materials, and/or lengthy and complicated procedures are required to obtain the desired products.

SUMMARY OF THE INVENTION

It is an object of the present invention to provide a one-step process for the highly selective preparation of an indole by using inexpensive starting materials.

According to the present invention, there is provided a process for the preparation of an indole which comprises reacting an aniline with a 1,2-glycol in the liquid phase in the presence of a catalyst containing metallic copper and/or copper oxide.

By way of example, the process of the present invention makes it possible to obtain indole by reacting aniline with ethylene glycol and to obtain 5-methylindole by reacting p-toluidine with ethylene glycol.

Thus, the process of the present invention has a number of advantages. First, the anilines and 1,2-glycols which can be used as the starting materials are very inexpensive. Second, the preparation of an indole from the starting materials can be achieved in a single step. Third, few by-products are formed and a very high selectivity is attained, so that an indole can be obtained in highly pure form. Fourth, compared with the vapor phase reaction, the amount of indoles produced per a unit amount of catalyst is high in the liquid phase reaction.

DETAILED DESCRIPTION OF THE INVENTION

The aniline used in the process of the present invention is a compound of the general formula

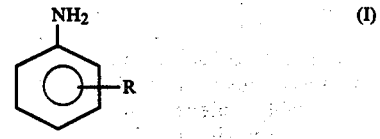

where R represents a hydrogen atom, halogen atom, hydroxyl group, alkyl group or alkoxy group. Specific examples thereof are aniline, o-toluidine, m-toluidine, p-toluidine, o-haloanilines, p-haloanilines, m-haloanilines, o-aminophenol, m-aminophenol, p-aminophenol, o-anisidine, m-anisidine, p-anisidine and the like.

The 1,2-glycol used in the process of the present invention is a member selected from the group consisting of ethylene glycol, propylene glycol, 1,2-butanediol, 1,2,4-butanetriol, glycerol, 2,3-butanediol, diethylene glycol and the like.

The process of the present invention is carried out in the presence of a catalyst containing metallic copper and/or copper oxide. That is, the catalyst contains metallic copper and/or copper oxide and, optionally, one or more other compounds.

More specifically, the catalysts which can be used in the process of the present invention are ones comprising metallic copper and/or copper oxide in such a form as powder, granules, masses, flakes, shaped pieces or the like; metallic copper and/or copper oxide supported on a carrier; a mixture of metallic copper and/or copper oxide and one or more other compounds; or such a mixture supported on a carrier.

The other compounds which can be used in combination with metallic copper and/or copper oxide include sulfates, carbonates, oxides, hydroxides of magnesium, calcium, strontium, barium, silver, zinc, aluminum, tin, iron, cobalt, nickel, chromium, manganese, titanium lead, molybdenum, silicon and the like; these metals in the elemental state; and the like.

The preferable catalysts are those which contain copper oxide and one or more oxides of silicon, zinc, manganese, magnesium, aluminum, chromium, titanium or iron, the amount of the copper oxide ranging preferably from 10 to 80%, more preferably, 20 to 70% based on the weight of the catalyst. More preferable catalysts are those which contain copper oxide, silicon oxide and one or more additional components selected from oxides of zinc, manganese, magnesium, aluminum or chromium, the amount of the copper oxide ranging preferably from 10 to 70%, more preferably, 15 to 60% based on the weight of the catalyst, and the amount of the silicon oxide ranging preferably from 10 to 70%, more preferably, 15 to 65% based on the weight of the catalyst. Examples of these catalysts include $CuO—SiO_2—MgO$, $CuO—SiO_2—ZnO$, $CuO—SiO_2—ZnO—MnO_2$, $CuO—SiO_2—ZnO—Cr_2O_3$ and the like.

The above-described catalysts can be prepared, for example, by the soaking method in which a carrier is soaked in an aqueous solution of a water-soluble copper salt, dried and then subjected to thermal decomposition. Alternatively, they can also be prepared by the coprecipitation method. For example, an alkali is added to a stirred aqueous solution of copper nitrate, magnesium nitrage, manganese nitrate and the like to coprecipitate copper, magnesium, manganese and the like. The precipitate so formed is separated by filtration, washed, dried and then calcined. The metal salts should be used in such amounts as to give the above-defined composition. Preferably, the precipitate is dried at room temperature for several to 24 hours, at temperatures of from 100° to 200° C. for 2 to 10 hours, or at temperatures of from 350° to 550° C. for 2 to 10 hours. When dried at temperatures of from 100° to 250° C., the precipitate is preferably pelletized prior to calcination.

As the carrier on which the catalytic substance of the present invention (i.e., metallic copper and/or copper oxide or a mixture of metallic copper and/or copper oxide and one or more other compounds) is supported, any materials that are in common use for supported catalysts can be used. However, diatomaceous earth, pumice, titania, silica-alumina, alumina, magnesia, silica gel, activated carbon, activated clay, asbestos and the like are used in typical cases.

Supported catalysts can be prepared by supporting the above-described catalytic substance on these carriers according to any conventional techniques. For example, they are prepared by soaking a carrier in an aqueous solution of a copper salt and, if necessary, other metal salts, drying the carrier until the water included therein is evaporated completely, and then calcining at a high temperature. No particular limitation is placed on the amount of catalytic substance supported on the carrier. Usually, depending on the type of carrier used, any suitable amount (for example, from 1 to 50%) of catalytic substance may be supported thereon.

Prior to the start of the reaction, the catalyst is usually subjected to a reduction treatment according to any conventional procedure. This is accomplished, for example, by heating the catalyst bed slowly with a mixture of hydrogen gas and nitrogen gas flowing therethrough and then keeping it at a temperature of from 200° to 300° C. for several hours.

In the present invention, the reaction is effected by heating a mixture of an aniline and a 1,2-glycol in the presence of at least one member selected from the above-described catalysts. In this case, various inert gaseous substances and/or solvents may coexist as diluents for the starting materials. The useful inert gaseous substances include, for example, nitrogen gas, hydrogen gas, carbon dioxide gas, water vapor and the vapors of compounds that are inert to this reaction. Hydrogen gas and mixtures of hydrogen gas with one or more of the above gases or vapors are preferred. The useful solvents include, for example, benzene, toluene, xylene, dioxane, pyridine, N-methylpyrrolidone, diphenylamine, triphenylamine and other organic solvents.

The process of the present invention can be carried out in a fixed-bed, fluidized-bed or moving-bed reactor or in a rotary or continuous reactor for liquid-phase reactions. However, no particular limitation is placed on the type of reactor used.

The amounts of aniline and 1,2-glycol used as the starting materials for this reaction should be such that from 0.05 to 5 moles and preferably from 0.1 to 2 moles of the 1,2-glycol is provided for each mole of the aniline.

No particular limitation is placed on the amount of catalyst used for this reaction. However, the catalyst is generally used in an amount of from 0.01 to 20 g and preferably from 0.1 to 10 g of the active component thereof per mole of the aniline used as one of the starting materials.

The reaction temperature should be in the range of from 200° to 500° C. and preferably from 250° to 400° C. If the reaction temperature is lower than 200° C., the reaction can hardly proceed, while if it is higher than 500° C., undesirably large amounts of by-products will be formed.

The reaction pressure may be selected from the pressures sufficient to maintain the liquid state of the reaction system. Preferably, the reaction pressure is a pressure below 150 $Kg/cm^2G$.

In various embodiments of the present invention, indole or a derivative thereof can readily be obtained in pure form by isolating it from the reaction product according to any conventional technique such as distillation.

The present invention is further illustrated by the following examples.

EXAMPLE 1

(1) Preparation of Catalyst:

500 ml of an aqueous solution containing 29.0 g of copper nitrate 3-hydrate, 15.4 g of magnesium nitrate 6-hydrate and 6.0 g of zinc nitrate 6-hydrate were added, under stirring, to 300 ml of an aqueous solution containing 32.5 g of water-glass (containing 37.0% by weight of $SiO_2$ and 17.6% by weight of $Na_2O$). The resulting mixture was adjusted to have a pH value of 6 to 8, heated to a temperature of 60° to 80° C. and was kept at that temperature for one hour to form and age a precipitate. The precipitate was decanted three times, filtered and washed with water. The precipitate was then dried at 130° C. for 10 hours. The resulting mass was pulverized to a catalyst containing $SiO_2$, ZnO, CuO and MgO.

(2) Activation of Catalyst:

The thus-obtained catalyst was activated by reducing it in a hydrogen stream at 350° C.

(3) Preparation of Indole:

93.1 g (1 mole) of aniline and 6.2 g (0.1 mole) of ethylene glycol as well as 3.0 g of the above catalyst were introduced into a stainless steel autoclave having an inner volume of 200 ml. The inside of the autoclave was purged with nitrogen gas and then hydrogen gas was fed to a gauge pressure of 10 kg/cm$^2$. The reaction was conducted under stirring, at 350° C. for one hour. The resulting reaction mixture was analyzed by gas chromatography. Thus, indole was obtained in a yield of 62.3% based on ethylene glycol.

EXAMPLES 2 TO 6

According to the same procedure as that described in Example 1, the catalysts shown in Table 1 were prepared and activated, and indole was produced. The results are tabulated in Table 1.

TABLE 1

| Example No. | Catalyst | Composition of Catalyst (ratio by weight) | Yield of Indole (based on ethylene glycol) |
|---|---|---|---|
| 2 | SiO$_2$—MgO—CuO | 50:30:20 | 53.5% |
| 3 | SiO$_2$—ZnO—CuO | 50:20:30 | 45.5% |
| 4 | SiO$_2$—ZnO—CuO—MnO$_2$ | 50:15:30:5 | 52.3% |
| 5 | SiO$_2$—ZnO—CuO—Cr$_2$O$_3$ | 30:20:40:10 | 47.6% |
| 6 | SiO$_2$—CuO | 50:50 | 19.4% |

EXAMPLE 7

(1) Preparation of Catalyst:

1,000 ml of an aqueous solution containing 23.05 g of 85% phosphoric acid were mixed with 500 ml of an aqueous solution containing 64.45 g of ZrOCl$_4$.8H$_2$O, 6.55 g of CuCl$_2$.2H$_2$O and then adjusted to a pH value of 5. The resulting mixture was heated under stirring, at a temperature of 60° to 80° C. for one hour to form and age a precipitate. After decanting three times, filtering and then washing by water the precipitate, it was dried at 130° C. for 10 hours to obtain a catalyst.

(2) Activation of Catalyst:

The above catalyst was activated according to the same procedure as that in Example 1.

(3) Preparation of Indole:

The same procedure as in Example 1 was repeated. Indole was obtained in a 21.3% yield based on ethylene glycol.

EXAMPLES 8 TO 10

The same procedure as in Example 1, except that the catalysts shown in Table 2 were used, was repeated to obtain the results tabulated in Table 2.

TABLE 2

| Example No. | Catalyst | Composition of Catalyst (ratio by weight) | Yield of Indole (based on ethylene glycol) |
|---|---|---|---|
| 8 | CuO | — | 11.0% |
| 9 | CuO—ZnO* | 50:50 | 6.1% |
| 10 | Raney-Cu | — | 5.2% |

*A catalyst named N-211 and supplied by JGC Corporation.

EXAMPLE 11

The same procedure as in Example 1, except that the reaction conditions were changed as shown in Table 3, was repeated to prepare indole. The results are tabulated in Table 3.

TABLE 3

| Reaction Temperature (°C.) | Reaction Time (hrs.) | Yield of Indole (based on ethylene glycol) |
|---|---|---|
| 250 | 5 | 11.3 |
| 300 | 1 | 49.8 |
| 400 | 0.5 | 38.4 |

EXAMPLES 12 TO 16

The same procedure as in Example 1, except that the starting anilines and 1,2-glycols shown in Table 4 were used, was repeated to prepare indoles. The results are tabulated in Table 4.

TABLE 4

| Starting Anilines | Starting 1,2-Glycols | Products | Yield Indoles (%) |
|---|---|---|---|
| p-toluidine | ethylene glycol | 5-methylindole | 34 |
| p-chloroaniline | " | 5-chloroindole | 51 |
| o-anisidine | " | 7-methoxyindole | 25 |
| aniline | propylene glycol | skatole | 53 |
| " | 1,2,4-butanetriol | triptophol | 15 |

What is claimed is:

1. A process for the preparation of indoles of the formula

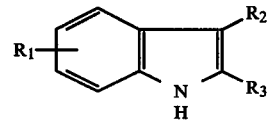

wherein, R$_1$ is a hydrogen atom, chlorine atom, bromine atom, methyl group, or methoxy group and R$_2$ and R$_3$ are a hydrogen atom, methyl group or ethyl group, at least one R$_2$ and R$_3$ being hydrogen; which comprises the step of reacting a compound selected from the group consisting of aniline, o-toluidine, m-toluidine, p-toluidine, o-chloroaniline, o-bromoaniline, m-chloroaniline, m-bromoaniline, p-chloroaniline, p-bromoaniline, o-anisidine, m-anisidine and p-anisidine, with a member selected from the group consisting of ethylene glycol, 1,2-propylene glycol, and 1,2-butanediol, in the presence of a catalytic amount of metallic copper or copper oxide or both, in an atmosphere of hydrogen or a mixture of hydrogen with nitrogen, hydrogen with carbon dioxide, or hydrogen with nitrogen and carbon dioxide, in the liquid phase at a temperature in the range of from 200° C. to 500° C.

2. A process as claimed in claim 1 wherein the catalyst consists of copper oxide and at least one oxide of silicon, zinc, manganese, magnesium, aluminum, chromium, titanium or iron.

3. A process as claimed in claim 1 wherein the catalyst consists of copper oxide, silicon oxide and at least one oxide of zinc, manganese, magnesium, aluminum or chromium.

4. A process as claimed in claim 3 wherein the catalyst consists of copper oxide in an amount of from 10 to 70% based on the weight of the catalyst and silicon oxide in an amount of from 10 to 70% based on the weight of the catalyst.

5. A process as claimed in claim 3 wherein the catalyst is a mixed oxide catalyst selected from CuO—Si- $O_2$—MgO, CuO—$SiO_2$—ZnO, CuO—$SiO_2$—ZnO—$MnO_2$ or Cu—$SiO_2$—ZnO—$Cr_2O_3$.

6. A process as claimed in claim 1 wherein the reaction is carried out in an atmosphere containing hydrogen gas.

7. A process as claimed in claim 1 wherein the reaction is carried out in the presence of water or water vapor.

8. A process as claimed in claim 1 wherein the reaction is carried out at a pressure of less than 150 kg/cm²G.

9. A process as claimed in claim 1 wherein the amount of the 1,2-glycol is 0.05 to 5 moles per each mole of the aniline.

* * * * *